United States Patent [19]

Cooper et al.

[11] Patent Number: 5,503,638

[45] Date of Patent: Apr. 2, 1996

[54] SOFT TISSUE STAPLING BUTTRESS

[75] Inventors: Joel Cooper, St. Louis, Mo.; Sally L. Winegar-Hentges, New Brighton, Minn.; Robert P. Nelson, Orono, Minn.; Kemal Schankereli, Stillwater, Minn.; Kristine M. Teich, Eden Prairie, Minn.

[73] Assignee: Bio-Vascular, Inc., St. Paul, Minn.

[21] Appl. No.: 194,382

[22] Filed: Feb. 10, 1994

[51] Int. Cl.$^6$ .................................................. A61F 2/02
[52] U.S. Cl. .................... 623/11; 623/2; 606/151; 606/148; 606/156; 606/232
[58] Field of Search ................ 623/2, 11; 606/76, 606/77, 220, 232, 151, 148, 149, 150, 156; 602/48, 50; 600/36, 37

[56] References Cited

U.S. PATENT DOCUMENTS

| | | |
|---|---|---|
| 2,143,910 | 1/1939 | Didusch . |
| 3,496,940 | 2/1970 | Steinman . |
| 3,633,582 | 1/1972 | Steinman . |
| 3,665,927 | 5/1972 | Kurtz ........................................ 606/231 |
| 3,739,402 | 6/1973 | Cooley et al. ................................ 623/2 |
| 3,983,581 | 10/1976 | Angell et al. ................................ 623/2 |
| 3,988,782 | 11/1976 | Dardik et al. . |
| 4,388,735 | 6/1983 | Ionescu et al. .............................. 623/2 |
| 4,648,881 | 3/1987 | Carpentier et al. . |
| 4,681,588 | 7/1987 | Ketharanathan . |
| 5,100,422 | 3/1987 | Berguer et al. . |
| 5,141,144 | 8/1992 | Foslien et al. . |
| 5,188,834 | 2/1993 | Grimm et al. . |
| 5,222,974 | 6/1993 | Kensey et al. . |

OTHER PUBLICATIONS

J. D. Cooper, et al, "Median Sternotomy for Bilateral Resection of Emphysematous Bullae", Journal of Thoracic Cardiovascular Sugery, 1981, vol. 82, pp. 892–897.
R. M. Juettner, et al. "Reinforced Staple Line in Severely Emphysematous Lungs", Journal of Thoracic Cardiovascular Surgery, 1989. vol. 97, pp. 362–363.
Japan Lung Surgery Journal,; 40 (10) 8(1826) pp. 1–5, (1992).
Connolly et al Journal of Thoracic Cardiovascula surgery; 1989, vol. 97 p. 361.

*Primary Examiner*—Paul Prebilic
*Attorney, Agent, or Firm*—Haugen and Nikolai

[57] ABSTRACT

A prosthetic article for surgical implantation within the body of a host in a surgical stapling procedure comprises a strip of host-tissue-compatible animal tissue material that is initially removably affixed between the spaced-apart legs a U-shaped buttress member to create a tubular configuration that can readily slip over the jaws of a conventional surgical stapler. When the staple gun is fired, the staples penetrate through the strips of animal tissue and the host tissue and thus serve to reinforce the staple line. Because the buttress member is releasibly attached to the strip of animal tissue, the buttress member can be readily separated and discarded following the firing of a staple gun.

8 Claims, 3 Drawing Sheets

```
┌─────────────────────────────────────────────────────────┐
│ CREATE SURGICAL ACCESS TO DISEASED TISSUE TO BE EX-     │
│ CISED.                                                  │
└─────────────────────────────────────────────────────────┘
                              │
┌─────────────────────────────────────────────────────────┐
│ COVER APPOSED SURFACES OF THE STAPLE CARTRIDGE SUP-     │
│ PORTING JAW AND ANVIL JAW OF A SURGICAL STAPLER WITH    │
│ STRIPS OF HOST COMPATIBLE XENOGENEIC TISSUE.            │
└─────────────────────────────────────────────────────────┘
                              │
┌─────────────────────────────────────────────────────────┐
│ POSITION THE COVERED JAWS OF THE SURGICAL STAPLE GUN    │
│ ABOUT THE TISSUE TO BE EXCISED.                         │
└─────────────────────────────────────────────────────────┘
                              │
┌─────────────────────────────────────────────────────────┐
│ FIRE THE STAPLE GUN TO EJECT ROWS OF STAPLES THROUGH    │
│ THE STRIPS OF XENOGENEIC TISSUE AND THE TISSUE TO BE    │
│ EXCISED AND AGAINST ITS ANVIL.                          │
└─────────────────────────────────────────────────────────┘
                              │
┌─────────────────────────────────────────────────────────┐
│ SEVER THE XENOGENEIC TISSUE AND HOST TISSUE ALONG A     │
│ STAPLE ROW.                                             │
└─────────────────────────────────────────────────────────┘
                              │
┌─────────────────────────────────────────────────────────┐
│ CLOSING THE SURGICALLY CREATED ACCESS.                  │
└─────────────────────────────────────────────────────────┘
```

*FIG. 3*

SOFT TISSUE STAPLING BUTTRESS

BACKGROUND OF THE INVENTION

1. Field of the Invention

This invention relates generally to a method and apparatus for improving a surgical procedure wherein staples are used to create an anastomosis or for closing the margins following removal of diseased tissue, and more particularly to an apparatus for reinforcing the staple line to prevent subsequent tearing of the tissue of fluid leakage, or, in the case of a pneumectomy, air leakage.

2. Discussion of the Prior Art

A frequent and troublesome complication following volume reduction surgery or other surgery performed on the lungs of patients suffering from bullous emphysema has been persistent air leaks which routinely occur and often last for several weeks. Even the smallest pinhole leak in lung tissue can result in a significant and prolonged air loss. In performing lung volume reduction surgery to improve the respiratory mechanics, a linear surgical stapler is often used to first place a plurality of staggered rows of closely spaced staples through the lung tissue at the margin between healthy and diseased tissue. The lung is then trimmed away along the outermost staple line or by dividing the tissue between staple lines. When using this procedure, and upon inflation of the lung, air leakage tends to occur not from the cut surface of the lung, but from the staple holes themselves which, being placed in severely emphysematous lung tissue, expand or tear as the lung is reinflated.

In the case of giant bullae, surgeons have previously utilized the averted wall of the incised bullae to reinforce the base of the staple line. This procedure is reported in a paper by J. D. Cooper, et al. entitled "Median Sternotomy for Bilateral Resection of Emphysematous Bullae" appearing in the *Journal of Thoracic Cardiovascular Surgery* in 1981, Vol. 82, pp. 892–897. Because the pathologic condition for which the volume reduction surgery is being performed seldom includes such giant bullae, a search continued for a suitable material for reinforcing the staple lines. Juettner and colleagues described use of a polydioxanone ribbon in conjunction with a TA type of stapling device. Here, reference is made to a paper captioned "Reinforced Staple Line in Severely Emphysematous Lungs", *J. Thorac. Cardiovasc. Surg.*, 1989: 97: 362–3. While the approach described therein works fairly well, the ribbon material does not cut easily with the knife embodied in the surgical stapler nor is it suitable for overlapping staple lines.

R. M. Peters reports in the *J. Thorac. Cardiovasc. Surg.*, 1989: 97: 361, the use of thin Teflon® felt, attached to the stapling device with adhesive strips. T. Nakamura et al. describe the use of a non-woven fabric of polyglycolic acid as a pledget for closing the bronchial stump, and as a patch for manually oversewing lung resection margins, *Japan Lung Surg. J.*, 1992: 40: (10) 1826.

The present invention is concerned with an improved article for use with a surgical staple gun for effectively reinforcing staple lines following removal of diseased tissue that not only reduce the incidence of tearing of the tissue at the staple line, but also, in the case of lung reduction surgery, greatly reduces the incidence of post-operative air leakage along the staples used to close the margins following removal of diseased lung tissue. While use of the present invention is being explained using lung surgery as the environment, the article of the present invention may also be used with staple guns having non-linear jaws, such as those designed to join bowel segments to preclude leakage.

SUMMARY OF THE INVENTION

In accordance with the present invention, a procedure for removing diseased tissue includes the steps of first providing a surgical staple gun having a pair of apposed jaws, one holding a cartridge of staples and the other being an anvil member against which the staples are to be fired. At the time of the surgery, a host tissue compatible xenogeneic or autogenic (hereinafter referred to simply as animal tissue) tissue strip, preferably formed from a suitably tanned piece of bovine, equine or other suitable animal pericardium or dura mater, is appropriately affixed to the apposed jaws of the surgical stapler. An opening is then created in the patient to expose the diseased tissue to be excised and the surgical staple gun with the animal tissue strips mounted thereon is then positioned such that the patient's tissue to be severed is disposed between the pair of jaws. When the staple gun is fired to simultaneously eject a plurality of rows of closely spaced staples from the cartridge, through the tanned animal tissue strips and the patient's own tissue and against the anvil member, the patient's tissue is effectively sandwiched between the animal tissue strips. Next, a reciprocating knife blade forming a part of the staple gun or a scalpel is employed to sever the animal tissue strips and the patient tissue along a line between the rows of staples. It is found that when glutaraldehyde-tanned bovine, equine, porcine, ovine, human pericardium or dura mater is used as the animal tissue strip material, it exhibits a self-closing property relative to the staples which are made to pierce it, thus, in the case of a pneumonectomy or other surgical procedures involving the lung, effectively sealing against the escape of air along the staple bodies.

In carrying out the above method in accordance with one embodiment, a tubular sleeve dimensioned to fit over and closely surround the jaws of the staple gun, are formed by fabricating a buttress member from a non-woven polyethylene material, such as is sold by the DuPont Company under its trademark, TYVEK®. A rectangular strip of this material is folded into a U-shape and a strip of tanned animal tissue of the type indicated is then attached, as by basting, to the apposed sides of the buttress member to form a closed tubular structure with the basted seams turned out. These tubular sleeves can then be readily slipped over the jaws of the staple gun with the animal tissue strips overlaying the operative cartridge and anvil surfaces of the staple gun. The sleeves are designed so that the tanned animal tissue strips will not readily rotate from the mating surface of the stapler jaw or slide off the stapler during use of the staple gun.

Following the stapling operation and before completing the surgical procedure, the filament used to attach the strip of animal tissue to the buttress is cut and removed, as is the buttress itself, leaving the tanned animal tissue strips behind reinforcing the staple line.

Using the method and article of manufacture of the present invention, bilateral multiple wedge excisions of both bullous and non-bullous areas of lung in patients with diffuse emphysema have been undertaken to improve pulmonary mechanics. Reinflation of the lung following the application of the staples under saline resulted in no identifiable air leakage along the staple line in most patients. As a result, hospitalization time has been significantly reduced for most patients. The use of the article of the present invention greatly reduces the amount of time required to position and hold the staple line reinforcing strips on the staple gun prior to its being fired.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 3 is a flow diagram describing the steps in the method in accordance with the present invention.

DESCRIPTION OF THE PREFERRED EMBODIMENT

Figure 1:
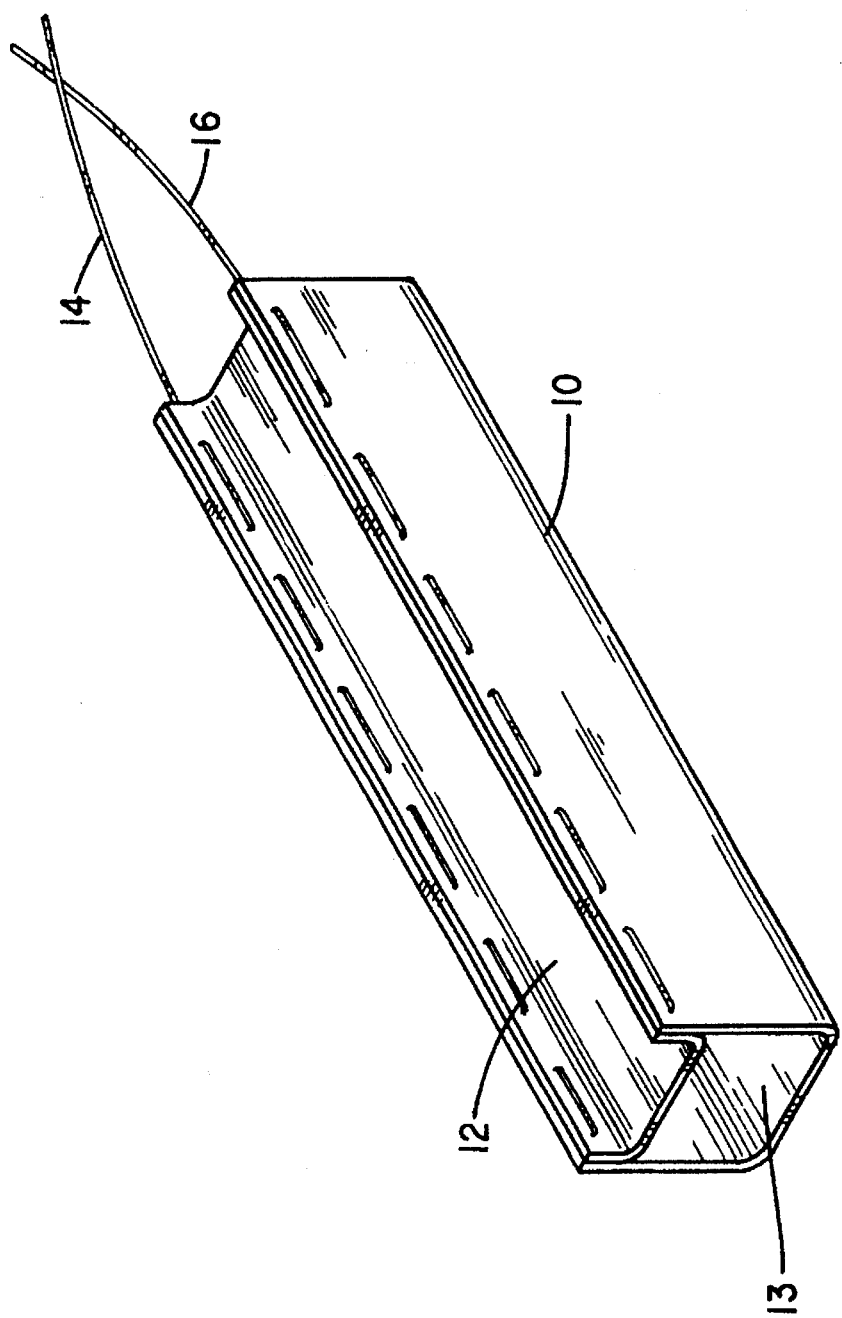
FIG. 1 is a perspective view of a preferred embodiment of the present invention.

Referring to FIG. 1, there is shown an article of manufacture constructed in accordance with one embodiment of the present invention for use in reinforcing a staple line in the course of a surgical procedure. It is seen to comprise a generally rectangular sheet or film of a flexible synthetic plastic material which is folded to provide a generally U-shaped buttress member 10. With no limitation intended, the film comprising the buttress member 10 may comprise a non-woven polyethylene sheet material, such as is sold by the DuPont Company under its trademark, Tyvek. The material is sterilizable and can be stored in a liquid, such as 1% propylene oxide in sterile water, prior to its use in surgery.

Supported between the generally parallel sides of the buttress 10 is a strip 12 of appropriately tanned tissue, a preferred material being cross-linked bovine, equine, porcine, ovine, human or other suitable animal pericardium or dura mater. One form of this material (bovine pericardium) is available from applicant's assignee and sold under its trademarks, PERI-GUARD® and SUPPLE PERI-GUARD™. In harvesting and treating the bovine pericardium material for use in humans, the material is cross-linked in a glutaraldehyde solution. The SUPPLE PERI-GUARD and PERI-GUARD material has been used in the past as a patch for use in hernia repair and pericardial closure following cardiac surgery in humans. Because bovine pericardium has a much higher density of collagen than most other connective tissues and contains substantially less non-collagenous tissue components such as smooth muscle and lipid and because the pericardium is crosslinked with glutaraldehyde further decreasing the antigenicity of the tissue, little or no inflammatory reaction in the adjoining tissue is apparent.

The strip 12 of tanned (cross-linked) animal tissue is temporarily fastened to its buttress member 10 by basting the two together along the free ends of the buttress 10 using filaments 14 and 16 as the stitch material. Without limitation, a polyethylene monofilament, such as 3.0 Prolene® suture material available through the Ethicon Div. of Johnson & Johnson Corp., provides excellent results.

Figure 2:
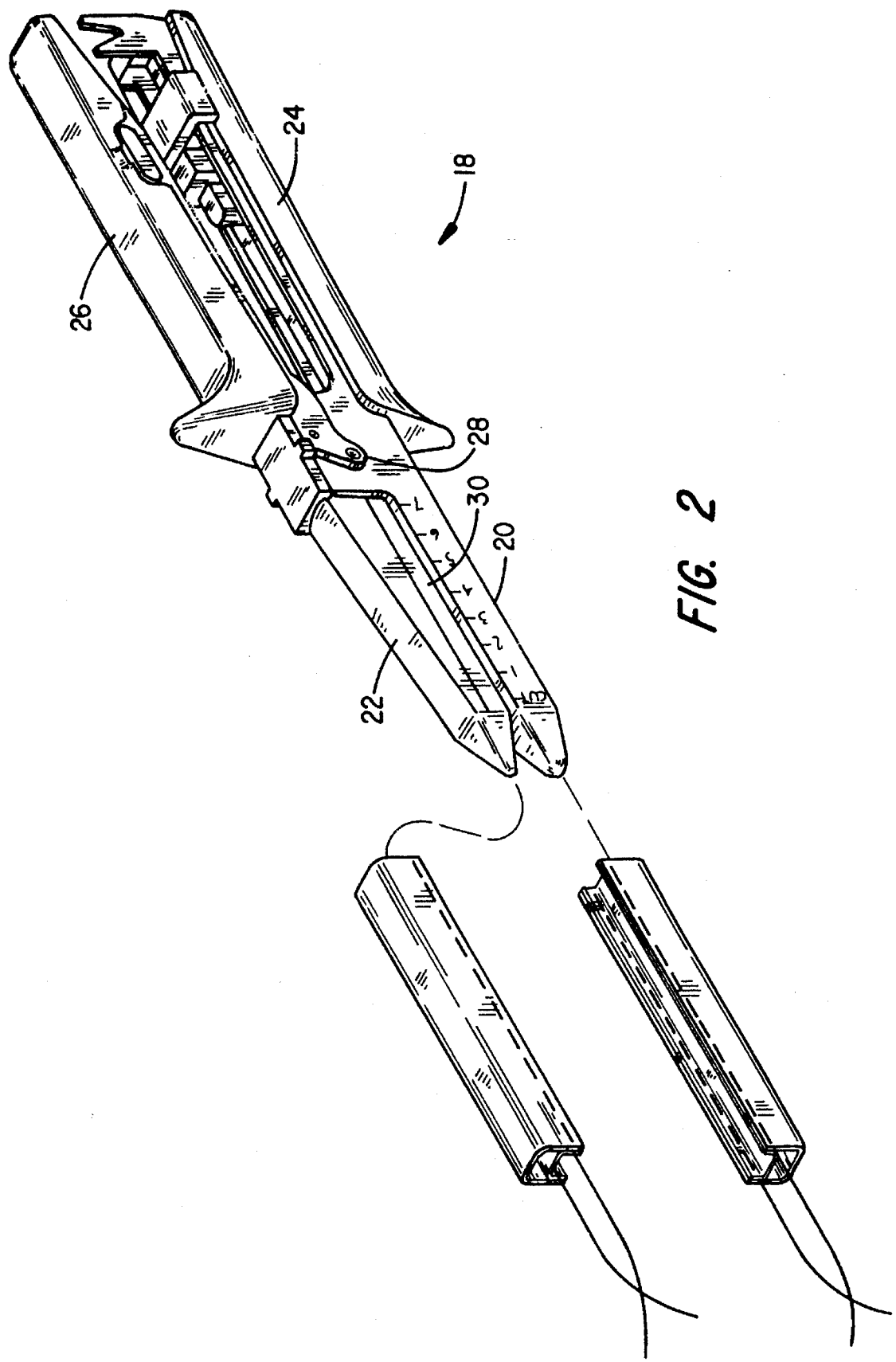
FIG. 2 shows the device of FIG. 1 positioned on a surgical stapler.

Referring now to FIG. 2, there is indicated generally by numeral 18 a surgical stapler. The particular surgical stapler illustrated is a Model ILA-75 disposable stapler available through the Healthcare Division of the 3M Company. It is to be understood, however, that the present invention can be used with surgical staplers other than those produced by the 3M Company and limitation to the device illustrated is not to be inferred. Those desiring more information concerning the construction and mode of operation of the surgical stapling device 18 are referred to U.S. Pat. No. 5,141,144 and the further patents referenced therein.

Irrespective of the particular model of surgical stapler involved in the practice of the present invention, it will generally have a staple cartridge supporting jaw 20 and an anvil supporting jaw 22 extending from a two-part handle including a stationary part 24 and a movable part 26 which is pivotally and removably hinged at 28 to the stationary part. The cartridge supporting jaw 20 holds a cartridge body (not shown) containing a plurality of staples disposed in rows oriented longitudinally to the jaw part 20 in opposition to the anvil 30 supported by jaw 22 when the members 24 and 26 are in their closed position.

The article depicted in FIG. 1 is dimensioned so that the longitudinal opening or lumen 13 thereof will receive one of the jaws 20 or 22 of the surgical stapler therein with the animal tissue strip 12 positioned against the staple cartridge of jaw 20 and the anvil 30 of the jaw 22. Because the article of the present invention comes in appropriate sizes, a close fit between the buttress member 10 and the exterior surface of the jaws over which it is fitted is achieved. The article of FIG. 1 is thus constrained from rotating about the jaw on which it is mounted, thereby insuring that the tanned animal tissue strip 12 will remain between the cooperating surfaces of the jaws 20 and 22 as the stapler jaws are made to engage the tissue to be stapled and later cut.

As indicated by the flow diagram of FIG. 3, in use, a surgeon will first create a surgical access to the diseased tissue to be excised. Next, the surgeon or surgical assistant will remove the articles of FIG. 1 from the container and sterile solution in which they are stored, rinse them in accordance with an existing protocol, and will slip two of the articles onto the apposed jaws of the surgical stapler 18 so that the apposed surfaces thereof are covered by the strips 12 of host compatible animal tissue. The surgeon will next position the covered jaws of the surgical staple gun 18 about the tissue to be excised. When so positioned, the surgeon next fires the staple gun to simultaneously eject multiple rows of closely spaced staples. The staples penetrate through the first layer 12 of animal tissue juxtaposed to the staple cartridge, thence through the host tissue and finally through the strip 12 of animal tissue covering the anvil. Upon striking the anvil, the staples are bent to close and tightly seal the tissue to be severed between the outer layers of animal tissue strips.

Surgical staple guns commonly incorporate a reciprocally movable blade that, when actuated by sliding a lever on the handle portion of the surgical stapler, causes a blade to traverse a line between adjacent rows of staples. This severs the tissue to be excised along a margin defined by one or more rows of staples. When used with the present invention, the blade also functions to longitudinally sever the two animal strips along with the patient's tissue. A standard scalpel may be used for this purpose if the staple gun does not incorporate a blade.

Following the actuation of the blade or scalpel, the surgeon or assistant will remove the basting filament 14, thus freeing the buttress 10 from the animal tissue strip and allowing it and the excised diseased tissue to be removed from the patient prior to closing.

Bovine pericardium, when tanned in accordance with manufacturing procedures used by applicant's assignee, as well as the other xenogeneic or autogenic tissues mentioned, exhibit a property of sealing or closing about an object made to pierce it. Thus, when the above procedure is used in a lung reduction surgery, the fact that the tanned animal tissue material closes about the staples, it creates a seal precluding air leaks.

While the article of the present invention serves to hold the animal tissue strip 12 against the cooperating faces of the jaws of the surgical stapler during positioning of the stapler on the tissue to be later severed and prior to firing of the staple gun, it can be appreciated that other ways of temporarily securing the tissue strips to the apposed faces of the stapler jaws are available. For example, a nontoxic biodegradable adhesive material may be applied to the apposed faces of the stapler or to one surface of the tanned animal tissue strip to hold that strip in place until the staple gun is fired. Also, suture loops passing through the tissue strips and arranged to fit over the jaws of the staple gun can act as a replacement for the buttress member 10. Moreover, while the staple gun and the stapling buttress illustrated in the drawings are generally linear, the invention is not to be construed as limited to that shape. Various other surgical staplers are on the market for use in various specialized surgical procedures having C-shaped or other anvil and staple cartridge support jaw shapes and those skilled in the art will envision how to construct buttresses of appropriate shape to conform to those other devices.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A prosthetic article for surgical implantation within a body of a host comprising:
   (a) a strip of host-tissue-compatible animal tissue material;
   (b) a buttress member of a generally U-shaped cross-section having a pair of integrally joined, spaced-apart leg segments; and
   (c) means for releasably securing the strip of animal tissue material to each of and between the pair of leg segments such that the buttress member is readily separable from the strip of animal tissue.

2. The article as in claim 1 wherein said strip of animal tissue material is cross-linked pericardium harvested from animals selected from the group consisting of equine, bovine, porcine, ovine and human animals.

3. The article as in claim 1 wherein said strip of animal tissue material is cross-linked dura mater harvested from animals selected from the group consisting of equine, bovine, porcine, ovine and human animals.

4. The article is in claim 1 wherein said strip of animal tissue material exhibits a property of sealing about an object piercing said strip.

5. The article as in any one of claims 1, 2, 3 or 4 wherein said buttress member comprises a flexible, sterilizable film sheet.

6. The article as in claim 5 wherein said film sheet is non-woven polyethylene.

7. The article as in claim 1 wherein said strip of animal tissue material is releasably secured to said buttress with a filament.

8. The article as in claim 7 wherein said filament is a polyethylene suture.

\* \* \* \* \*